US00PP27856P3

(12) United States Plant Patent van Kleinwee

(10) Patent No.: US PP27,856 P3
(45) Date of Patent: Apr. 4, 2017

(54) *PETUNIA* PLANT NAMED 'PEHY0014'

(50) Latin Name: *Petunia hybrida*
Varietal Denomination: PEHY0014

(71) Applicant: SYNGENTA PARTICIPATIONS AG, Basel (CH)

(72) Inventor: Theodorus Cornelis van Kleinwee, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/998,448

(22) Filed: Jan. 5, 2016

(65) Prior Publication Data

US 2016/0198614 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.13

(58) Field of Classification Search
USPC ..... Plt./356.13
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0014' particularly distinguished by the large, violet-purple flowers with white margins, deep green foliage, good branching, early flowering, a semi-upright habit and is floriferous throughout the season.

1 Drawing Sheet

Latin name of the genus and species of the plant claimed: *Petunia hybrida.*

Varietal denomination: 'PEHY0014'.

BACKGROUND OF THE NEW PLANT

The present invention comprises a new *Petunia*, botanically known as *Petunia hybrida*, and hereinafter referred to by the variety name 'PEHY0014'.

'PEHY0014' is a product of a planned breeding program. The new cultivar has large, violet-purple flowers with white margins, deep green foliage, good branching, a semi-upright habit, early flowering, and floriferous throughout the season.

'PEHY0014' originated from a hybridization made in October 2010 in a controlled breeding environment in Enkhuizen, Netherlands. The female parent was the unpatented proprietary plant designated 'P0189' with purple flower color and white margin, smaller flower size, and much later to flower.

The male parent of 'PEHY0014' was an unpatented proprietary plant identified as 'N0338-1' with very large, purple with white margin flowers, a plant with low vigor and poor branching.

The resulting seeds were sown in February 2011. 'PEHY0014' was selected as a single flowering plant within the progeny of the stated cross May 25, 2011 in a controlled environment in Enkhuizen, Netherlands.

The first act of asexual reproduction of 'PEHY0014' was accomplished when vegetative cuttings were propagated from the initial selection in June 2011 in a controlled environment in Enkhuizen, Netherlands.

BRIEF SUMMARY OF INVENTION

Horticultural examination of plants grown from cuttings of the plant initiated in September 2011 in Angers, France, and continuing thereafter, has demonstrated that the combination of characteristics as herein disclosed for 'PEHY0014' are firmly fixed and are retained through successive generations of asexual reproduction.

'PEHY0014' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Jun. 27, 2014, No. 2014/1722. 'PEHY0014' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
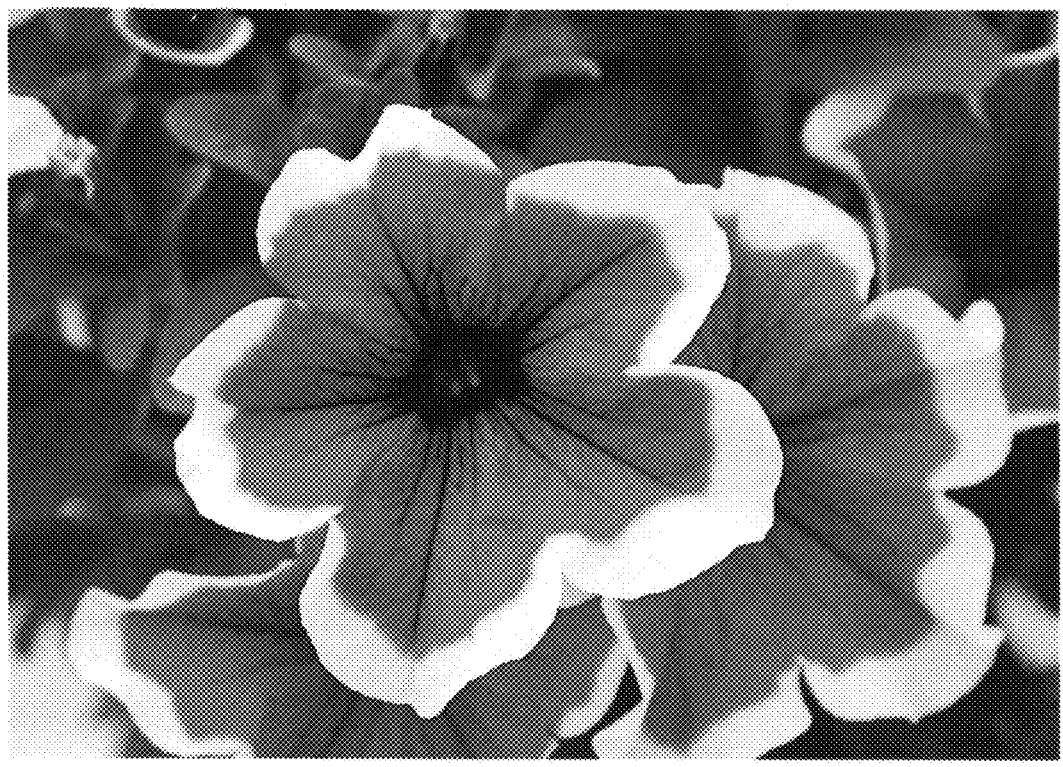
Figure 2:
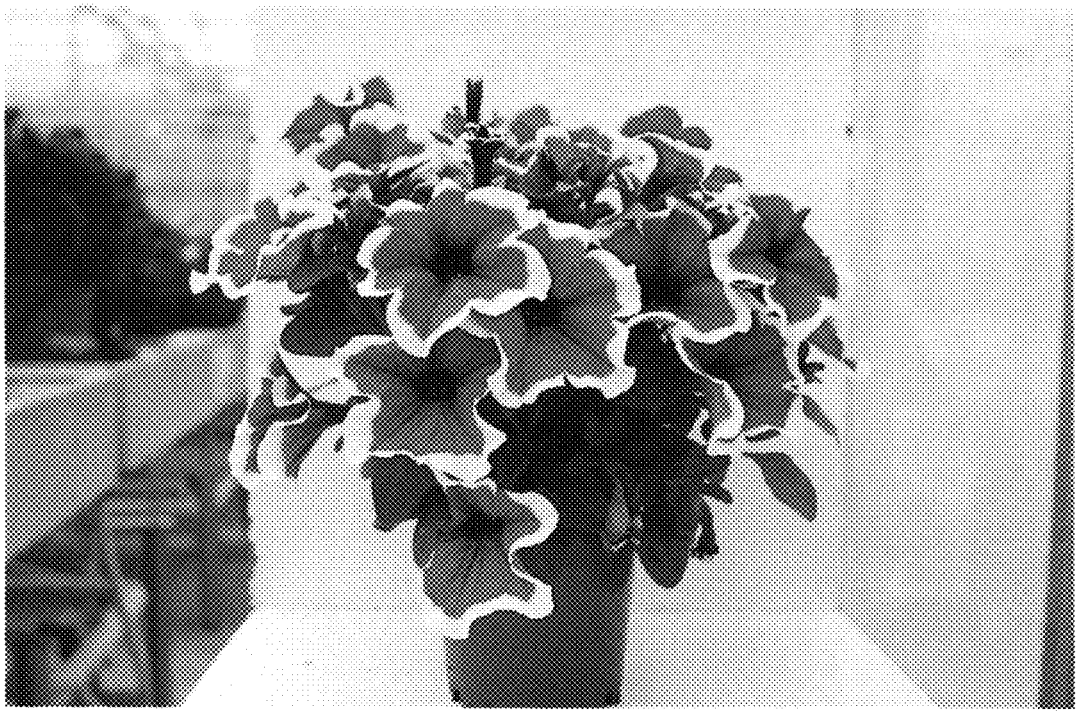

The accompanying photographic drawing shows typical flower and foliage characteristics of 'PEHY0014' with colors being as true as possible with an illustration of this type. The photographic drawing shows in FIG. 2. a flowering plant of the new variety and in FIG. 1. a close-up of the flowers.

DETAILED BOTANICAL DESCRIPTION

The plant descriptions and measurements were taken around Oct. 1, 2014, from plants grown for breeding purposes in a greenhouse in Enkhuizen, Netherlands. The plants had been planted around Jul. 10, 2014. They were approximately 12 weeks of age and growing in 19 cm containers. They had been cut back a few weeks before the observations.

The aforementioned photographs were taken in April 2014 from plants growing in a greenhouse trial in Andijk, Netherlands. These plants were approximately 12-13 weeks of age.

Color references are made to The Royal Horticultural Society Colour Chart (R.H.S.) 2001.

TABLE 1

DIFFERENCES BETWEEN THE NEW VARIETY 'PEHY0014' AND A SIMILAR VARIETY

| | 'PEHY0014' | 'FORTUNIA PURPLE PICOTEE' |
|---|---|---|
| Flower color: | Between the tones of RHS N74A and RHS N78B with white edge | RHS 79B and white |
| Flowering response: | Earlier | Later |
| Aspect of leaves: | A little twisted | Flat |

Plant:

*Form, growth and habit.*—Semi-upright, free branching, free flowering, big flowers.

*Plant height.*—15 cm.

*Plant height (inflorescence included).*—20 cm.

*Plant width.*—36 cm.

Roots:

*Number of days to initiate roots.*—About 12 days at about 22 degrees C.

*Number of days to produce a rooted cutting plant.*—18-24 days at about 22 degrees C.

*Type.*—Fine, fibrous, free branching.

*Color.*—RHS N155B.

Foliage:

*Arrangement of leaves.*—Simple, opposite, sometimes decussate.

*Immature leaf, color upper surface.*—RHS 138A.

*Immature leaf, color lower surface.*—Intermediate between the tones of RHS 138A and RHS 144A.

*Mature leaf, color, upper surface.*—RHS 137B.

*Mature leaf, color lower surface.*—RHS 146B.

*Length.*—8-9 cm.

*Width.*—4-5 cm.

*Shape.*—Ovate.

*Base shape.*—Attenuate.

*Apex shape.*—Obtuse.

*Margin.*—Entire.

*Texture, upper surface.*—Pubescent.

*Texture, lower surface.*—Pubescent.

*Color of veins, upper surface.*—RHS 144B.

*Color of veins, lower surface.*—RHS 144B.

*Petiole color.*—RHS 144B.

*Length.*—0.7 cm.

*Diameter.*—0.5 cm.

*Texture.*—Hirsute.

Stem:

*Quantity of main branches per plant.*—6.

*Color of stem.*—RHS 144A.

*Length of stem.*—15-20 cm.

*Diameter.*—0.5 cm.

*Length of internodes.*—3-4 cm.

*Texture.*—Hirsute with glandular hair.

*Color of pedicels.*—RHS 144C.

*Length.*—3-5 cm.

*Diameter.*—0.2 cm.

*Texture.*—Hirsute.

Inflorescence:

*Type of inflorescence.*—Single flowers, emerging from the upper nodes of the stem.

*Blooming habit.*—Continuous flowering throughout the summer months, little affected by heat.

*Start of flowering.*—About 8 weeks from planting rooted cuttings.

*Quantity of flowers per plant.*—About 15-20.

*Lastingness of individual blooms on the plant.*—Up to 14 days depending on temperature.

*Fragrance.*—None.

Bud (just when opening/showing color):

*Color.*—From the base to the top: Mainly RHS N79A to RHS N79B, and a few weak, green macules, RHS 143C; at the tip. RHS 150D, cream.

*Length.*—4.5 cm.

*Width.*—1.7 cm.

*Shape.*—Oblong.

Immature flower:

*Flower, horizontal diameter.*—Approximately 6 cm.

*Flower, vertical diameter.*—3.7 cm.

*Color, upper surface.*—Deep purple red, between RHS N74A and RHS N78A, and a white margin of 0.5 cm width.

*Color, lower surface.*—RHS N82A and white at the edges.

Mature flower:

*Shape.*—Salver-shape, with funnel shape base, formed by 5 fused petals.

*Flower, horizontal diameter.*—6.8-7.3 cm.

*Flower, vertical diameter.*—4.5 cm.

*Color upper surface.*—Deep purple red, between the tones of RHS N74A and RHS N78B, and a white edge of 1 cm width; dark veins of weak to medium distinctness.

*Color lower surface.*—RHS N82A.

*Petal apex shape.*—Shallow mucronulate.

*Petal base shape.*—Fused.

*Petal margin.*—Entire, wavy.

*Waviness of petals margin.*—Medium.

*Petal lobation.*—Weak to medium.

*Petal texture, upper surface.*—Papillose, glabrous.

*Petal texture, lower surface.*—Papillose, glabrous near apex, hirsute near base.

*Corolla tube, color inner side.*—RHS 83A, with dense black veins.

*Corolla tube, color outer side.*—RHS 77B.

*Corolla tube, length.*—3-3.5 cm.

*Corolla tube, diameter.*—1.3 cm.

*Corolla, texture.*—Hirsute.

Calyx:

*Form.*—5 sepals in a whorl, fused at the base.

*Color, upper surface.*—RHS 147B.

*Color, lower surface.*—RHS 138A-B.

*Shape of sepal.*—Oblanceolate.

*Sepal length.*—2.8 cm.

*Sepal width.*—1.7 cm.

*Apex shape.*—Rounded.

*Base.*—Fused.

*Margins.*—Entire.

*Texture, upper surface.*—Hirsute.

*Texture, lower surface.*—Hirsute.

Reproductive organs:

*Gynoecium.*—Pistil: 1. Length: 2.3 cm. Style color: RHS N144A. Style length: 2 cm. Stigma color: RHS 145A on the lower side, upper side is 143A. Stigma shape: Flat, oval disc. Ovary color: RHS 144A.

*Androecium*.—Number of stamens: 5. Color of filaments: RHS 145C. Length filaments: 1.8-2.2 cm. Anther color: RHS 160B. Anther length: 0.1 cm. Anther shape: Elliptical. Color of pollen: RHS 160C. Pollen amount: Plenty.

Fertility/seed set: Has not been observed on this hybrid.

Disease/pest resistance: Has not been observed on this hybrid.

What is claimed is:

1. A new and distinct variety of *Petunia* plant named 'PEHY0014' substantially as illustrated and described herein.

* * * * *